US010400446B2

(12) United States Patent
Takeuchi et al.

(10) Patent No.: US 10,400,446 B2
(45) Date of Patent: Sep. 3, 2019

(54) TRANSPARENT NONCOMBUSTIBLE SHEET

(71) Applicant: UNITIKA LTD., Hyogo (JP)

(72) Inventors: Nobutaka Takeuchi, Osaka (JP); Hitoshi Kourogi, Osaka (JP); Yuki Horikoshi, Osaka (JP)

(73) Assignee: UNITIKA LTD. (JP)

(*) Notice: Subject to any disclaimer, the term of this patent is extended or adjusted under 35 U.S.C. 154(b) by 165 days.

(21) Appl. No.: 14/914,045

(22) PCT Filed: Aug. 26, 2014

(86) PCT No.: PCT/JP2014/072276
§ 371 (c)(1),
(2) Date: Feb. 24, 2016

(87) PCT Pub. No.: WO2015/029992
PCT Pub. Date: Mar. 5, 2015

(65) Prior Publication Data
US 2016/0208483 A1  Jul. 21, 2016

(30) Foreign Application Priority Data

Aug. 26, 2013 (JP) .................................. 2013-174727

(51) Int. Cl.
*D06M 15/233* (2006.01)
*D06M 15/263* (2006.01)
(Continued)

(52) U.S. Cl.
CPC ............. *E04B 1/946* (2013.01); *A47H 23/08* (2013.01); *B32B 5/024* (2013.01); *B32B 5/028* (2013.01);
(Continued)

(58) Field of Classification Search
CPC ........... D06M 2200/30; D06M 15/233; D06M 15/263; D06M 15/327; D06M 2101/00;
(Continued)

(56) References Cited

U.S. PATENT DOCUMENTS 4,344,906 A    8/1982 Kitagawa et al.

FOREIGN PATENT DOCUMENTS

JP      55-31822 A      3/1980
JP      05-123869 A     5/1993
(Continued)

OTHER PUBLICATIONS

International Search Report for PCT/JP2014/072276 dated Dec. 2, 2014.

*Primary Examiner* — Camie S Thompson
(74) *Attorney, Agent, or Firm* — McDonald Hopkins LLC (57) ABSTRACT

The present invention addresses the problem of providing a transparent, noncombustible sheet having excellent transparency but minimized blurring and color bleeding. The means for addressing the problem is a transparent noncombustible sheet including a glass fiber fabric and a cured resin composition layer impregnated into the glass fiber fabric; wherein, the cured resin composition layer is formed by curing a resin composition including a curable resin and a bifunctional (meth)acrylate, total light transmittance of the transparent noncombustible sheet being no less than 80%, and haze of the transparent noncombustible sheet being no more than 30%.

18 Claims, 2 Drawing Sheets

(51) Int. Cl.
   *B32B 5/02* (2006.01)
   *B32B 5/26* (2006.01)
   *G01N 21/59* (2006.01)
   *B32B 27/30* (2006.01)
   *E04B 1/94* (2006.01)
   *A47H 23/08* (2006.01)
   *B32B 27/12* (2006.01)
   *D06M 15/327* (2006.01)
   *G01N 21/84* (2006.01)
   *D06M 101/00* (2006.01)

(52) U.S. Cl.
   CPC ............... *B32B 5/26* (2013.01); *B32B 27/12* (2013.01); *B32B 27/304* (2013.01); *D06M 15/233* (2013.01); *D06M 15/263* (2013.01); *D06M 15/327* (2013.01); *E04B 1/941* (2013.01); *G01N 21/59* (2013.01); *G01N 21/84* (2013.01); *B32B 2250/40* (2013.01); *B32B 2260/021* (2013.01); *B32B 2260/023* (2013.01); *B32B 2260/046* (2013.01); *B32B 2262/101* (2013.01); *B32B 2307/3065* (2013.01); *B32B 2307/412* (2013.01); *B32B 2457/208* (2013.01); *B32B 2607/00* (2013.01); *D06M 2101/00* (2013.01); *D06M 2200/30* (2013.01)

(58) Field of Classification Search
   CPC .......... E04B 1/941; E04B 1/946; E04B 1/046; G01N 21/59; B32B 2260/023; B32B 2260/046; B32B 2307/3065; B32B 2307/412; B32B 2457/208; B32B 2607/00; B32B 5/024; B32B 5/028; B32B 2262/101; B32B 2250/40; B32B 2260/021; B32B 27/12; B32B 5/026; C08J 5/043; C08J 5/24
   USPC ...... 428/292.1, 441, 500, 300.1, 320.5, 325; 524/492, 494, 553, 554
   See application file for complete search history.

(56) References Cited

FOREIGN PATENT DOCUMENTS

| | | | |
|---|---|---|---|
| JP | 06-173557 A | | 6/1994 |
| JP | 2005-319746 A | | 11/2005 |
| JP | 2011-213093 A | | 10/2011 |
| JP | 2013-129766 | * | 7/2013 |
| JP | 2013-154550 | * | 8/2013 |
| JP | 2013-154550 A | | 8/2013 |
| WO | WO2011037083 | * | 3/2011 |
| WO | 2013/094585 A1 | | 6/2013 |
| WO | WO2013094585 | * | 6/2013 |

* cited by examiner

TRANSPARENT NONCOMBUSTIBLE SHEET

CROSS-REFERENCE TO RELATED APPLICATION

This application is a 35 U.S.C. 371 national stage filing of PCT Application No. PCT/JP2014/072276, filed on Aug. 26, 2014, which claims the benefit of Japanese Patent Application No. 2013-174727, filed on Aug. 26, 2013, both of which are incorporated herein in their entirety by reference.

TECHNICAL FIELD

The present invention relates to a transparent noncombustible sheet. Furthermore, the present invention relates to a smoke-proof hanging wall, a smoke-proof shutter, a partition wall, a smoke-proof curtain and a touch panel which are prepared with the transparent noncombustible sheet.

BACKGROUND ART

The Building Standards Act and Enforcement Ordinance of Building Standards Act stipulate that smoke eliminating equipment should be installed for the purpose of inhibiting the flow of smoke, a poisonous gas, and the like generated at the time of a fire in the building to enable emergency evacuation and fire fighting activities to be smoothly performed. Accordingly, there are many cases in which a smoke-proof hanging wall and the like, as smoke eliminating equipment and smoke shielding equipment, are installed in the building such as an office building and commercial facilities.

The smoke-proof hanging wall is usually attached to the ceiling of a building for the purpose of temporarily obstructing smoke, a poisonous gas, and the like on the occurrence of a fire from flowing through a passageway and toward an upper layer story to secure the time required for emergency evacuation and the like. As such, in order that a visual field is not interrupted by a smoke-proof hanging wall and the beautiful appearance is not impaired, as the smoke-proof hanging wall, a sheet of transparent plate glass, a transparent resin composite of glass fiber and a resin, or the like has been used. The transparent resin composite of glass fiber and a resin is advantageously hard to break as compared with the transparent plate glass. For example, Patent Document 1 discloses a smoke-proof hanging wall composed of a transparent noncombustible sheet including glass fiber woven fabric and a cured resin layer.

Moreover, at a gateway of a factory, a warehouse or the like, a sheet shutter which is raised or lowered at the time of use is often installed. Such a sheet shutter is often constituted of a transparent resin-made sheet and a skeletal frame so as to allow an object to be visually confirmed through the sheet shutter when lowered (for example, see Patent Document 2). By imparting smoke-proof properties to such a sheet shutter, on the occurrence of a fire, an effect of suppressing the flow of smoke and the like can be expected. On that account, there is a possibility that such a sheet shutter disclosed in Patent Document 1 is used as a smoke-proof shutter.

PRIOR ART DOCUMENTS

Patent Documents

Patent Document 1: Japanese Patent Laid-open Publication No. 2005-319746

Patent Document 2: Japanese Patent Laid-open Publication No. 06-173557

SUMMARY OF THE INVENTION

Although such a transparent noncombustible sheet disclosed in Patent Document 1, for example, can be enhanced in transparency, the view through the transparent noncombustible sheet is liable to be blurred, and moreover, color bleeding is easily generated due to light from a fluorescent lamp. As such, when such a sheet is used as a smoke-proof hanging wall or the like, there is a problem that a visual field is interrupted and the beautiful appearance is easily impaired. Moreover, with regard to the sheet shutter disclosed in Patent Document 2, since the transparent resin-made sheet is constituted of transparent vinyl chloride, smoke-proof properties can be exhibited but there is a problem that the sheet is poor in noncombustibility.

Under such circumstances, a main object of the present invention is to provide a transparent noncombustible sheet that has a high transparency, and furthermore, can suppress blurring and color bleeding. Furthermore, the present invention is also aimed at providing a smoke-proof hanging wall, a smoke-proof shutter, a partition wall, a smoke-proof curtain and a touch panel which are prepared with the transparent noncombustible sheet. In this connection, "having a high transparency" refers to having a total light transmittance greater than or equal to 80% and a haze value less than or equal to 30%. Moreover, in the present invention, "blurring" refers to the phenomenon in which a view through a transparent noncombustible sheet is blurred, and "color bleeding" refers to the phenomenon in which colors such as red and blue bleed when a transparent noncombustible sheet irradiated with light from a fluorescent lamp located behind the sheet is visually observed.

The present inventors have conducted diligent studies in view of solving such problems mentioned above. As a result, it has been found that, in the transparent noncombustible sheet disclosed in Patent Document 1, there is no blurring immediately after the production, but with the lapse of time (for example, at the end of 1 week or so), the glass fiber pattern becomes conspicuous while values of total light transmittance and haze are (that is, a high level of transparency is) maintained, and finally, the phenomenon in which a view through the sheet is blurred is caused. Moreover, in the transparent noncombustible sheet disclosed in Patent Document 1, it has also been found that color bleeding becomes conspicuous with the lapse of time after the completion of the production. For example, in the case where the transparent noncombustible sheet disclosed in Patent Document 1 is used as a smoke-proof hanging wall, since the smoke-proof hanging wall is installed to the ceiling and suspended down from the ceiling by 50 cm or so, there occurs a problem that color bleeding is liable to become conspicuous due to light from a fluorescent lamp installed on the ceiling and the beautiful appearance is impaired. The present inventors consider the reason that blurring and color bleeding are conspicuous in the transparent noncombustible sheet disclosed in Patent Document 1 as follows. That is, in the transparent noncombustible sheet disclosed in Patent Document 1, the difference in refractive index between a glass composition and a resin composition lies within a specific range to enhance the transparency and the difference in Abbe number between the glass composition and the resin composition lies within a specific range to reduce the scattering in the visible light region. However, the refractive index is generally measured at a specific wavelength, and the Abbe number is generally calculated on the basis of refractive indices of light at three different specific wavelengths from a calculation formula. Accordingly, the present inventors consider that, even if the difference in refractive index and the difference in Abbe number lie within the specific ranges in the first place, it is difficult to take into consideration refractive indices of a glass composition and a resin composition at all wavelengths in the visible light region, and shrinkage of the resin composition with time easily occurs at the interface between the glass composition and the resin composition, resulting in the occurrence of blurring and color bleeding. And then, as a result of further diligent studies, the present inventors have found that a transparent noncombustible sheet including glass fiber fabric and a cured resin composition layer prepared by allowing the glass fiber fabric to be impregnated with a resin composition, wherein the cured resin composition layer is formed of a cured product of the resin composition containing a curable resin and a bifunctional (meth)acrylate, the total light transmittance of the transparent noncombustible sheet is greater than or equal to 80%, and the haze value of the transparent noncombustible sheet is less than or equal to 30% has high transparency and also can suppress blurring and color bleeding. Based on these findings, the present inventors have conducted further studies, and thus, the present invention has been completed.

That is, the present invention provides the invention of embodiments set forth below.

Item 1. A transparent noncombustible sheet including glass fiber fabric and a cured resin composition layer prepared by allowing the glass fiber fabric to be impregnated with a resin composition, wherein the cured resin composition layer is formed of a cured product of the resin composition containing a curable resin and a bifunctional (meth)acrylate, the total light transmittance of the transparent noncombustible sheet is greater than or equal to 80%, and the haze value of the transparent noncombustible sheet is less than or equal to 30%.

Item 2. The transparent noncombustible sheet described in the item 1, wherein the bifunctional (meth)acrylate is a di(meth)acrylate of an alkylene diol with 1 to 6 carbon atoms.

Item 3. The transparent noncombustible sheet described in the item 1 or 2, wherein the molecular weight of the bifunctional (meth)acrylate is less than or equal to 250.

Item 4. The transparent noncombustible sheet described in the item 3, wherein the molecular weight of the bifunctional (meth)acrylate is greater than or equal to 150.

Item 5. The transparent noncombustible sheet described in any one of the items 1 to 4, wherein the resin composition contains a styrene monomer.

Item 6. The transparent noncombustible sheet described in any one of the items 1 to 5, wherein the resin composition is photocurable.

Item 7. The transparent noncombustible sheet described in any one of the items 1 to 6, wherein the resin composition contains 40 to 80% by mass of the curable resin and 10 to 40% by mass of the bifunctional (meth)acrylate.

Item 8. The transparent noncombustible sheet described in any one of the items 1 to 6, wherein the resin composition contains 60 to 80% by mass of the curable resin and 10 to 20% by mass of the bifunctional (meth)acrylate.

Item 9. The transparent noncombustible sheet described in any one of the items 1 to 8, wherein the proportion of the glass fiber fabric in the total amount of the glass fiber fabric and the cured resin composition layer is 20 to 50% by mass.

Item 10. The transparent noncombustible sheet described in any one of the items 1 to 8, wherein the proportion of the glass fiber fabric in the total amount of the glass fiber fabric and the cured resin composition layer is 20 to 28% by mass.

Item 11. The transparent noncombustible sheet described in any one of the items 1 to 10, further including a film layer disposed on the cured resin composition layer.

Item 12. The transparent noncombustible sheet described in the item 11, further including a net body layer which is composed of a glass fiber net body and interposed between the cured resin composition layer and the film layer.

Item 13. The transparent noncombustible sheet described in any one of the items 1 to 12, wherein the transparent noncombustible sheet has a thickness of 40 to 400 µ.m.

Item 14. The transparent noncombustible sheet described in any one of the items 1 to 13, wherein two pieces of glass fiber fabric are arranged at respective surface sides of the cured resin composition layer while the center part in the thickness direction of the piece of glass fiber fabric is positioned nearer to the surface side than the center part in the thickness direction of the cured resin composition layer.

Item 15. The transparent noncombustible sheet described in any one of the items 1 to 14, wherein a plurality of pieces of glass fiber fabric are included in the identical cured resin composition layer, at least two pieces of glass fiber fabric among the plurality of pieces of glass fiber fabric are arranged at least at respective surface sides of the cured resin composition layer, and the two pieces of glass fiber fabric are included at respective surface sides of the cured resin composition layer while the shortest distance $L_1$ from the surface of the cured resin composition layer to the center part of the piece of glass fiber fabric and the thickness $L_0$ of the cured resin composition layer satisfy the relationship of the following equation (I):

$$0(\%) < L_1/L_0 \times 100 < 30(\%) \qquad (I).$$

Item 16. A smoke-proof hanging wall including the transparent noncombustible sheet described in any one of the items 1 to 15.

Item 17. A smoke-proof shutter including the transparent noncombustible sheet described in any one of the items 1 to 15.

Item 18. A partition wall including the transparent noncombustible sheet described in any one of the items 1 to 15.

Item 19. A smoke-proof curtain including the transparent noncombustible sheet described in any one of the items 1 to 15.

Item 20. A touch panel including the transparent noncombustible sheet described in any one of the items 1 to 15.

Item 21. A use of a transparent noncombustible sheet as a smoke-proof hanging wall being attached to and suspended down from the ceiling of a building, the transparent noncombustible sheet including glass fiber fabric and a cured resin composition layer prepared by allowing the glass fiber fabric to be impregnated with a resin composition, wherein the cured resin composition layer is formed of a cured product of the resin composition containing a curable resin and a bifunctional (meth)acrylate, the total light transmittance of the transparent noncombustible sheet is greater than or equal to 80%, and the haze value of the transparent noncombustible sheet is less than or equal to 30%.

Item 22. A construction method of a transparent noncombustible sheet for a smoke-proof hanging wall, the method including:

step I of:

employing transparent noncombustible sheets as candidate sheets each comprising glass fiber fabric and a cured resin composition layer prepared by allowing the glass fiber fabric to be impregnated with a resin composition; and selecting a transparent noncombustible sheet among the candidate sheets, the selected transparent noncombustible sheet including the cured resin composition layer formed of a cured product of the resin composition containing a curable resin and a bifunctional (meth)acrylate, having a total light transmittance of the transparent noncombustible sheet of greater than or equal to 80% and having a haze value of the transparent noncombustible sheet of less than or equal to 30%; and step II of allowing the candidate sheet selected in the step I to be attached to and suspended down from the ceiling of a building.

Item 23. A screening method of a transparent noncombustible sheet for a smoke-proof hanging wall, the method including:

a first step of:
  employing transparent noncombustible sheets as candidate sheets, the transparent noncombustible sheets each comprising glass fiber fabric and a cured resin composition layer prepared by allowing the glass fiber fabric to be impregnated with a resin composition, the cured resin composition layer being formed of a cured product of the resin composition containing a curable resin and a bifunctional (meth)acrylate; and
  measuring the total light transmittance and the haze value of the candidate sheets; and
a second step of selecting a candidate sheet as a transparent noncombustible sheet for a smoke-proof hanging wall, the selected candidate sheet having a total light transmittance measured in the first step of greater than or equal to 80% and having a haze value measured in the first step of less than or equal to 30%.

Advantages of the Invention

According to the transparent noncombustible sheet of the present invention, it is possible to provide a transparent noncombustible sheet that has a high transparency and can suppress blurring and color bleeding. Since the transparent noncombustible sheet according to the present invention has high transparency and also can suppress blurring and color bleeding, the transparent noncombustible sheet can be suitably used as a smoke-proof hanging wall, a smoke-proof shutter, a partition wall, a smoke-proof curtain, a touch panel, or the like.

EMBODIMENTS OF THE INVENTION

1. Transparent Noncombustible Sheet

The transparent noncombustible sheet according to the present invention is characterized as including glass fiber fabric and a cured resin composition layer prepared by allowing the glass fiber fabric to be impregnated with a resin composition, wherein the cured resin composition layer is formed of a cured product of the resin composition containing a curable resin and a bifunctional (meth)acrylate, the total light transmittance of the transparent noncombustible sheet is greater than or equal to 80%, and the haze value of the transparent noncombustible sheet is less than or equal to 30%. In this connection, in the present invention, "(meth) acrylate" means "acrylate" or "methacrylate".

Figure 1:
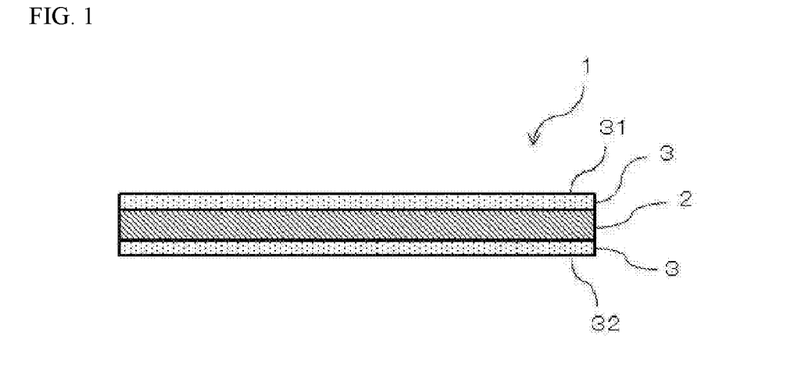
FIG. 1 is a schematic sectional view of the transparent noncombustible sheet according to the present invention.
Figure 4:
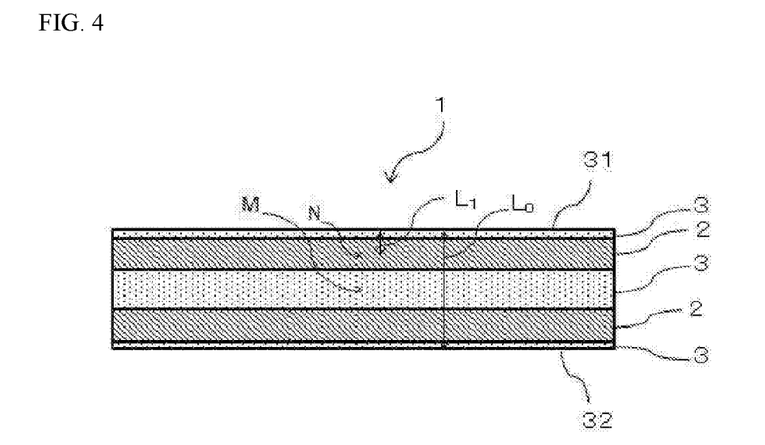
FIG. 4 is a schematic sectional view of the transparent noncombustible sheet according to the present invention.

For example, as shown in FIG. 1, a transparent noncombustible sheet 1 according to the present invention has a layered structure including a piece of glass fiber fabric 2 and a cured resin composition layer 3 prepared by allowing the glass fiber fabric 2 to be impregnated with a resin composition. In the transparent noncombustible sheet 1, at least one layer of glass fiber fabric 2 needs to be included and a plurality of layers thereof may be included. For example, as shown in FIG. 4, in the transparent noncombustible sheet 1 according to the present invention, two pieces of glass fiber fabric 2 may be arranged so as to be positioned at respective surface sides of the cured resin composition layer 3.

In FIG. 1, the cured resin composition layer 3 is prepared by allowing interstices among a plurality of glass fibers constituting the glass fiber fabric 2 to be filled with a resin composition, and one surface side portion 31 of the cured resin composition layer 3 and the other surface side portion 32 thereof communicate with each other through the interstice part. Moreover, in the transparent noncombustible sheet 1 according to the present invention, from the viewpoint of enhancing the transparency and suppressing the blurring and the color bleeding, for example as shown in FIGS. 1 to 4, it is preferred that a portion of the cured resin composition layer 3 be formed on at least one face of a layer of glass fiber fabric 2, and it is more preferred that two portions of the cured resin composition layer 3 be formed on respective faces of a layer of glass fiber fabric 2.

Figure 2:
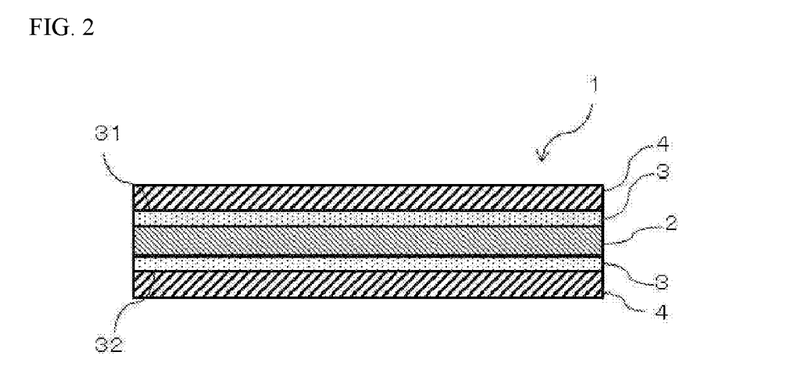
FIG. 2 is a schematic sectional view of the transparent noncombustible sheet according to the present invention.
Figure 3:
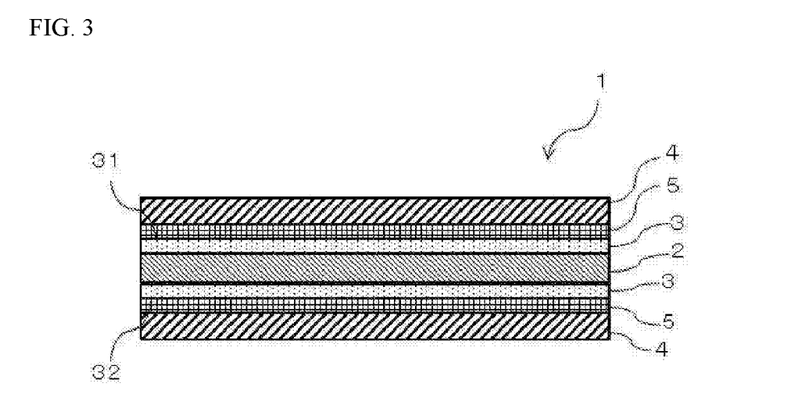
FIG. 3 is a schematic sectional view of the transparent noncombustible sheet according to the present invention.

In the transparent noncombustible sheet 1 according to the present invention, for example as shown in FIG. 2 and FIG. 3, for the purposes of enhancing the noncombustibility of the transparent noncombustible sheet 1, improving the mechanical strength (hardness) and the like, a film layer 4 may be layered on the cured resin composition layer 3 as necessary. Moreover, as shown in FIG. 3, for the purposes of improving the mechanical strength (hardness) of the transparent noncombustible sheet 1 and the like, a net body layer 5 composed of glass fibers may be interposed between the cured resin composition layer 3 and the film layer 4 as necessary. Each of the film layer 4 and the net body layer 5 may be layered on one face side of the layer of glass fiber fabric 2, and as shown in FIG. 2 and FIG. 3, may be layered on both face sides of the layer of glass fiber fabric 2. Hereinafter, the composition of respective layers constituting the transparent noncombustible sheet 1 according to the present invention will be described in detail.

In the transparent noncombustible sheet 1 according to the present invention, the cured resin composition layer 3 is prepared by allowing the glass fiber fabric 2 described below to be impregnated with a resin composition and is formed of a cured product of the resin composition containing a curable resin and a bifunctional (meth)acrylate. As the curable resin, one which can be crosslinked with a bifunctional (meth)acrylate is preferred, and examples thereof include a curable resin having an unsaturated group such as a vinyl group and a (meth)acrylate group. Specific examples of the curable resin having an unsaturated group include a vinyl ester resin (an epoxy acrylate resin), a urethane acrylate resin, a fluorene acrylate resin, an unsaturated polyester resin, and the like. Of these, a vinyl ester resin, a urethane acrylate resin, a fluorene acrylate resin and the like, which are curable resins having an unsaturated group that serves as a crosslinking point at the end of the molecular chain, are especially preferred for the following reasons. That is, the shrinkage on curing by crosslinking is reduced, and as a result, a high level of continuity of the interface between glass fiber described below and the cured resin composition is presumably maintained, and the sheet can easily suppress blurring and color bleeding.

The proportion of the curable resin in the resin composition forming the cured resin composition layer 3 is not particularly limited, and for example, the proportion is preferably 40 to 80% by mass or so, and from the viewpoint of suppressing the blurring, the proportion is more preferably 60 to 80% by mass or so. In this connection, in the case where the resin composition contains a resin other than the curable resin, it is preferred that the proportion of the resin other than the curable resin in the resin composition be less than or equal to 20% by mass.

In the present invention, the bifunctional (meth)acrylate contained in the resin composition mentioned above has two (meth)acrylate groups in its molecule and allows the curable resin to be crosslinked with the (meth)acrylate group when energy such as light (e.g. ultraviolet rays) and heat is given thereto to form the cured resin composition layer 3.

In the present invention, since the cured resin composition layer 3 is formed of a cured product of the resin composition containing a curable resin and a bifunctional (meth)acrylate, by allowing the glass fiber fabric 2 described below to be impregnated with the resin composition, it is possible to constitute a transparent noncombustible sheet which has high transparency and also can suppress blurring and color bleeding. On the other hand, if a bifunctional (meth)acrylate is not used in the resin composition forming the cured resin composition layer 3, although it is possible to enhance the transparency, sometimes blurring and color bleeding cannot be suppressed. In the configuration of the present invention, although the details of the mechanism to enable the transparent noncombustible sheet to have high transparency and also suppress blurring and color bleeding by using a bifunctional (meth)acrylate have not yet been elucidated, for example, the reason is presumed to be as follows. That is, it is thought that, in the transparent noncombustible sheet 1 according to the present invention, since the cured resin composition layer 3 is formed of a cured product of the resin composition containing a curable resin and a bifunctional (meth)acrylate, the shrinkage of the curable resin with time is suppressed by virtue of the bifunctional (meth)acrylate, a high level of continuity of the interface between glass fiber described below and the cured resin composition is maintained, and as a result, blurring and color bleeding attributed to the lowering in continuity of such an interface are suppressed.

Examples of the bifunctional (meth)acrylate preferably include a di(meth)acrylate of an alkylene diol with 1 to 6 carbon atoms, and the like. With this, it is possible to enhance the transparency of the transparent noncombustible sheet 1 according to the present invention and to more effectively suppress the blurring and color bleeding. Although the details of the reason for this have not necessarily been elucidated yet, it is thought that this is attributed to the interface between glass fiber and the cured resin composition where the curable resin can be more densely crosslinked since the molecular chain of the alkylene diol component in the molecule of a di(meth)acrylate of an alkylene diol with 1 to 6 carbon atoms is short.

Furthermore, as the bifunctional (meth)acrylate, especially preferred is a di(meth)acrylate of an alkylene diol with 1 to 6 carbon atoms in which the carbon chain of the alkylene diol has a branched structure. With this, it is possible to enhance the transparency of the transparent noncombustible sheet 1 according to the present invention and to more effectively suppress the blurring and color bleeding. Although the details of the reason for this have not necessarily been elucidated yet, it is thought that this is attributed to the interface between glass fiber described below and the cured resin composition where a high level of interface continuity is especially effectively maintained by virtue of the more shortened molecular chain of the alkylene diol component along with the more enhanced reactivity with the curable resin.

Moreover, from the viewpoint similar to the above, it is preferred that the molecular weight of a bifunctional (meth)acrylate be less than or equal to 250. Moreover, the molecular weight of a bifunctional (meth)acrylate is preferably greater than or equal to 150 and more preferably greater than or equal to 200.

Specific examples of the bifunctional (meth)acrylate preferably include 1,3-butylene glycol diacrylate (molecular weight 198), 1,4-butanediol diacrylate (molecular weight 198), 1,5-pentanediol diacrylate (molecular weight 212), 1,6-hexanediol diacrylate (molecular weight 226), diethylene glycol diacrylate (molecular weight 214), dipropylene glycol diacrylate (molecular weight 242), neopentyl glycol diacrylate (molecular weight 212), 1,3-butylene glycol dimethacrylate (molecular weight 226), 1,4-butanediol dimethacrylate (molecular weight 226), 1,5-pentanediol dimethacrylate (molecular weight 240), diethylene glycol dimethacrylate (molecular weight 242), neopentyl glycol dimethacrylate (molecular weight 240) and the like. Of these, preferable examples in which the carbon chain of the alkylene diol has a branched structure include 1,3-butylene glycol diacrylate, dipropylene glycol diacrylate, neopentyl glycol diacrylate, 1,3-butylene glycol dimethacrylate, neopentyl glycol dimethacrylate, and the like. One kind of bifunctional (meth)acrylate may be used alone, and two or more kinds thereof may be used in combination.

In the presence of a curable resin, the bifunctional (meth)acrylate functions as a curing agent which allows the curable resin to be cured while energy such as light and heat is given thereto. It is preferred that the bifunctional (meth)acrylate be a photocuring agent which allows the curable resin to be cured when irradiated with light such as ultraviolet rays. In this case, the resin composition forming the cured resin composition layer 3 is photocurable.

The proportion of the bifunctional (meth)acrylate in the resin composition is not particularly limited, and for example, the proportion is 10 to 40% by mass or so, and from the viewpoint of suppressing the blurring, the proportion is preferably 10 to 20% by mass or so.

The resin composition forming the cured resin composition layer 3 may contain a styrene monomer from the viewpoints of the adjustment of refractive index and the like. If a styrene monomer is contained therein, the viscosity of the resin composition is easy to adjust. The proportion of the styrene monomer in the resin composition is not particularly limited, and for example, the proportion is 0 to 40% by mass, preferably 10 to 40% by mass or so and more preferably 15 to 30% by mass or so.

The resin composition forming the cured resin composition layer 3 may further contain additives such as a combust retardant, an ultraviolet ray absorber, a filler and an antistatic agent. Examples of the combust retardant include aluminum hydroxide, magnesium hydroxide, trichloroethyl phosphate, triallyl phosphate, ammonium polyphosphate, phosphoric acid ester, and the like. Examples of the ultraviolet ray absorber include benzotriazole and the like. Examples of the filler include calcium carbonate, silica, talc and the like. Examples of the antistatic agent include a surfactant and the like. One kind of these additives may be used alone and two or more kinds thereof may be used in combination.

In the present invention, in order to suppress a visual field from being interrupted and the beautiful appearance from being impaired when the transparent noncombustible sheet 1 is used as a smoke-proof hanging wall, a smoke-proof sheet or the like, refractive indices of the glass fiber fabric 2 described below and the cured resin composition 3 are set so as to be approximated to each other. From such a viewpoint, the refractive index of the cured resin composition 3 is preferably 1.45 to 1.65 or so and more preferably 1.50 to 1.60 or so.

In the transparent noncombustible sheet 1 according to the present invention, the glass fiber fabric 2 is constituted of a plurality of glass fibers. In the glass fiber fabric 2, the plurality of glass fibers are entangled with one another to form a piece of fabric. Examples of the glass fiber fabric 2 include glass fiber woven fabric (glass cloth) constituted of a plurality of warp yarns and a plurality of weft yarns. The weave of the glass fiber woven fabric is not particularly limited, and examples thereof include a plain weave, a sateen weave, a twill weave, a basket weave, a rib weave, and the like. Although the fabric density of glass fiber woven fabric is not particularly limited, a fabric density of greater than or equal to 60 yarns/25 mm is preferred for example, because a large through-hole is not formed in the glass fiber fabric 2, and the excellent noncombustible performance is maintained even in the case where the cured resin composition of the transparent noncombustible sheet 1 has combusted.

The glass material of the glass fiber constituting the glass fiber fabric 2 is not particularly limited, and for example, a known glass material can be used. Examples of the glass material include alkali-free glass (E-glass), acid-resistant alkali glass (C-glass), high-strength/high-modulus glass (S-glass, T-glass or the like), alkali-resistant glass (AR glass) and the like, and preferably include highly versatile alkali-free glass (E-glass). The glass fibers constituting the glass fiber fabric 2 may be fibers composed of one kind of glass material and may be fibers prepared by combining two or more kinds of glass fibers which are made of different glass materials.

The yarn number count of the glass fiber constituting the glass fiber fabric 2 is not limited to a specific one as long as the glass fiber fabric 2 can be formed. From the viewpoint of increasing the fabric density, for example, the yarn number count of the glass fiber is preferably less than or equal to 20 tex. One kind of the yarn number count of the glass fiber may be selected alone and two or more kinds thereof may be combined. In this connection, the tex count of the glass fiber corresponds to the number of grams per 1000 m.

As the glass fiber constituting the glass fiber fabric 2, preferred is a glass yarn prepared by twisting and uniting a plurality of numbers of single fibers which are continuous glass fibers. The number of single fibers in the glass yarn is preferably 30 to 400 or so and more preferably 40 to 120 or so. Moreover, the diameter of the single fiber in the glass yarn is preferably 3.0 to 6.0 μm or so and more preferably 3.0 to 5.0 μm or so from the viewpoint of suppressing the color bleeding of the transparent noncombustible sheet 1. The yarn number count of the glass yarn is preferably 3 to 30 tex, more preferably 3 to 12 tex and further preferably 3 to 5 tex from the viewpoint of suppressing the color bleeding. Although the details of the mechanism in which the color bleeding of the transparent noncombustible sheet 1 is suppressed with use of the glass fiber fabric 2 that includes the glass yarn having the single fiber diameter and the yarn number count within the ranges mentioned above have not yet been elucidated, it is thought that, when such conditions are satisfied, the shrinkage in the interface between the glass yarn and the cured resin composition layer 3 is effectively suppressed, and as a result, color bleeding of the transparent noncombustible sheet 1 is suppressed.

From the viewpoints of improving the adhesivity between the glass fiber fabric 2 and the cured resin composition layer 3 and enhancing the durability of the transparent noncombustible sheet 1 according to the present invention, it is preferred that the surface of the glass fiber constituting the glass fiber fabric 2 be subjected to a surface treatment with a silane coupling agent.

In the transparent noncombustible sheet 1, from the viewpoint of suppressing the color bleeding, the proportion (% by mass) of the glass fiber fabric 2 is preferably 20 to 50% by mass and more preferably 20 to 28% by mass in the total amount of the glass fiber fabric 2 and the cured resin composition layer 3 described below. Moreover, the mass ($g/m^2$) of a piece of glass fiber fabric 2 is preferably 10 to 120 ($g/m^2$), more preferably 10 to 60 ($g/m^2$) and further preferably 10 to 40 ($g/m^2$).

As described above, at least one layer of glass fiber fabric 2 needs only to be included and a plurality of layers thereof may be included. In this context, in the case where a plurality of layers of glass fiber fabric 2 are included, for example as shown in FIG. 4, it is preferred that two pieces of glass fiber fabric 2 be arranged at respective surface sides (31 side and 32 side in FIG. 4) of the cured resin composition layer 3 while the center part N in the thickness direction of the piece of glass fiber fabric 2 is positioned nearer to the surface side than the center part M in the thickness direction of the cured resin composition layer 3. In this way, with two pieces of glass fiber fabric 2 positioned at respective surface sides (31 side and 32 side in FIG. 4) of the cured resin composition layer 3, as compared with a transparent noncombustible sheet in which the glass fiber fabric 2 is arranged only near the center part in the thickness direction of the cured resin composition layer 3, it is possible to improve the mechanical strength (hardness) and furthermore it is possible to more effectively suppress the warpage caused by heat. More specifically, it is preferred that the shortest distance $L_1$ from the surface of the cured resin composition layer 3 to the center part N of the piece of glass fiber fabric 2 and the thickness $L_0$ of the cured resin composition layer 3 satisfy the relationship of the following equation (I).

$$0\% < L_1/L_0 \times 100 < 30\% \qquad (I)$$

Moreover, it is especially preferred that two pieces of glass fiber fabric 2 be included at respective surface sides of the cured resin composition layer 3 while $L_1$ and $L_0$ satisfy the relationship of the equation (I). Further specifically, it is preferred that a plurality of pieces of glass fiber fabric 2 be included in the identical cured resin composition layer 3, at least two pieces of glass fiber fabric 2 among the plurality of pieces of glass fiber fabric 2 be arranged at least at respective surface sides of the cured resin composition layer 3, and the two pieces of glass fiber fabric 2 be included at respective surface sides of the cured resin composition layer 3 while the shortest distance $L_1$ from the surface of the cured resin composition layer 3 to the center part of the piece of glass fiber fabric 2 and the thickness $L_0$ of the cured resin composition layer 3 satisfy the relationship of the foregoing equation (I). Furthermore, it is more preferred that the $L_1$ and the $L_0$ satisfy $10\ (\%) < L_1/L_0 \times 100 < 20\ (\%)$.

Moreover, in the case where two pieces of glass fiber fabric 2 are arranged at respective surface sides of the cured resin composition layer 3 while the center part N in the thickness direction of the piece of glass fiber fabric 2 is positioned nearer to the surface side than the center part M in the thickness direction of the cured resin composition layer 3, and furthermore, in the case where the proportion of the glass fiber fabric 2 in the transparent noncombustible sheet 1 is set to 20 to 28 (% by mass) and the mass of a piece of glass fiber fabric 2 is set to 10 to 40 (g/m²) as described below, a transparent noncombustible sheet excellent especially in inhibitory effect on color bleeding is attained with the aid of an effect of the transparent noncombustible sheet 1 of easily suppressing color bleeding caused by deformation thereof.

The difference in refractive index between the glass fiber fabric 2 and the cured resin composition 3 described below is preferably less than or equal to 0.05 and more preferably less than or equal to 0.02. The refractive index of the glass fiber fabric 2 is preferably 1.45 to 1.65 or so and more preferably 1.50 to 1.60 or so.

In this connection, the refractive index of the above-mentioned glass fiber fabric 2 is measured in accordance with the B method in JIS K 7142: 2008. Specifically, with regard to glass fibers constituting the glass fiber fabric 2, the measurement is performed at 23° C. using methylene iodide ($n_D^{23}$ 1.747), butyl phthalate ($n_D^{23}$ 1.491) and dimethyl carbonate ($n_D^{23}$ 1.366) as the immersion liquid, using the NAR-2T available from ATAGO CO., LTD. as an Abbe refractometer and using the sodium D line with a wavelength of 589 nm as a light source, and an average value of measured values obtained from the test repeated 5 times is defined as the value of refractive index. Moreover, the refractive index of the cured resin composition 3 is measured in accordance with the B method in JIS K 7142: 2008. Specifically, the cured resin composition is pulverized, the measurement is performed at 23° C. using methylene iodide ($n_D^{23}$ 1.747), butyl phthalate ($n_D^{23}$ 1.491) and dimethyl carbonate ($n_D^{23}$ 1.366) as the immersion liquid, using the downsized measuring microscope STM5-311 (available from Olympus Corporation, the observation magnification of 400 magnifications) as a microscope and using the sodium D line with a wavelength of 589 nm as a light source, and an average value of measured values obtained from the test repeated 5 times is defined as the value of refractive index.

For example, the thickness of a piece of glass fiber fabric 2 is 10 to 100 μm or so, and from the viewpoint of suppressing the color bleeding, the thickness is preferably 10 to 55 μm and more preferably 10 to 35 μm or so. In the case where the thickness of a piece of glass fiber fabric 2 is set to 10 to 35 μm, it is especially preferred that the glass volume fraction calculated according to the following equation (II) be greater than or equal to 38%. For example, the piece of glass fiber fabric 2 which has a thickness of 10 to 35 μm and a volume fraction greater than or equal to 38% is obtained by subjecting glass fibers to a fiber-opening treatment.

$$\text{Glass volume (\%)} = (A/(B \times C)) \times 100 \qquad \text{(II)}$$

A: Mass (g/m²) of glass fiber fabric
B: Specific gravity (g/m³) of glass material constituting glass fiber fabric
C: Thickness (m) of a piece of glass fiber fabric For the purpose of enhancing the noncombustibility, improving the mechanical strength or the like, the transparent noncombustible sheet 1 according to the present invention may further include a film layer 4 disposed on the cured resin composition layer 3, as necessary. The resin (resin film) constituting the film layer 4 is not particularly limited, and examples thereof preferably include a combust-retardant synthetic resin such as a vinyl chloride resin, and the like. In this connection, with regard to the resin constituting the film layer 4, the resin itself may have combust retardancy and the resin may be a resin allowed to have combust retardancy by being blended with a combust retardant and the like. In the present invention, the film layer 4 can enhance the weather resistance of the transparent noncombustible sheet 1 and prevent the damage thereof due to contact with another object, the film layer 4 can also function as a protective layer. It is preferred that the transparent noncombustible sheet 1 according to the present invention have two film layers 4 at respective surface sides.

In the case where the transparent noncombustible sheet 1 according to the present invention has the film layer 4, the thickness of the film layer 4 is not particularly limited, and for example, the thickness is 50 to 200 μm or so and preferably 80 to 150 μm or so.

For the purpose of enhancing the noncombustibility, improving the mechanical strength or the like, the transparent noncombustible sheet 1 according to the present invention may further include a net body layer 5 which is composed of a glass fiber net body and interposed between the cured resin composition layer 3 and the film layer 4, as necessary. The glass fiber net body constituting the net body layer 5 is not particularly limited, and a net body made of the same glass fiber as the glass fiber described in the section of the glass fiber fabric 2 can be exemplified. Moreover, the shape and the structure of the glass fiber net body are not particularly limited, and examples of the glass fiber net body include a cross-laminated glass fibers-made net in which each of weft yarns is sandwiched between two warp yarns and fixed by a resin, and the like. In the net body layer 5, by allowing the opening width between glass fibers to be set to preferably 3 to 20 mm, it is possible to secure a high level of transparency of the transparent noncombustible sheet 1, and furthermore, light can be obtained satisfactorily through the opening between glass fibers and the strength of the whole transparent noncombustible sheet 1 can be improved. From the viewpoint of enhancing the noncombustibility or improving the mechanical strength, it is preferred that the transparent noncombustible sheet 1 according to the present invention have two net body layers 5 at respective surface sides.

In the case where the transparent noncombustible sheet 1 according to the present invention has the net body layer 5, the thickness of the net body layer 5 is not particularly limited, and for example, the thickness is 50 to 300 μm or so and preferably 100 to 200 μm or so.

The transparent noncombustible sheet 1 of the present invention has a high level of transparency in order to suppress a visual field from being interrupted and the beautiful appearance from being impaired when the transparent noncombustible sheet 1 is used as a smoke-proof hanging wall, a smoke-proof shutter, a partition wall, a smoke-proof curtain (for example, one used in a factory or the like), a touch panel or the like. For example, as described above, the smoke-proof hanging wall is used by being installed to the ceiling of a building and suspended down from the ceiling by 50 cm or so, and in the case of being low in transparency, the beautiful appearance is liable to be impaired. From the viewpoint of ensuring a high level of transparency, the total light transmittance of the transparent noncombustible sheet 1 according to the present invention is greater than or equal to 80% and preferably greater than or equal to 85%. Moreover, the haze value of the transparent noncombustible sheet 1 according to the present invention is less than or equal to 30%, preferably less than or equal to 20% and more preferably less than or equal to 10%. Each of the total light transmittance and haze of the transparent noncombustible sheet 1 is a value obtained by measurement according to JIS K7375 2008 "Plastics—Determination of total luminous transmittance and reflectance".

In the transparent noncombustible sheet 1 according to the present invention, it is preferred that the difference between the Abbe number of the cured resin composition and the Abbe number of the glass fiber be less than or equal to 40, and it is more preferred that the difference therebetween be less than or equal to 30. By allowing the difference in refractive index between the glass fiber fabric 2 and the cured resin composition layer 3 to be less than or equal to 0.02, the difference in Abbe number is easily allowed to become less than or equal to 40. In this connection, the Abbe numbers of the cured resin composition and the glass fiber are measured in the following manner.

(Abbe Number of Cured Resin Composition)

A sheet of a cured resin composition containing no glass fiber fabric with the same thickness as that of a sheet of a cured resin composition containing glass fiber fabric is prepared under the same condition as that in the case of containing glass fiber fabric, the sheet is formed into a specimen with a size of 8 mm in width by 20 mm in length, the surface thereof is polished well, and the sheet is measured for the refractive index at a wavelength of 589 nm in accordance with the JIS K 7142A method under the condition where the NAR-2T available from ATAGO CO., LTD. as an Abbe refractometer, diiodomethane as the contact liquid and the sodium D line with a wavelength of 589 nm as a light source are used and the measurement temperature is set to 23° C. Subsequently, natural light is used as a light source, a dispersion value is measured to be calculated, and the Abbe number is calculated according to the following equation (III).

$$\text{Abbe number} = (\text{Refractive index at wavelength of } 589 \text{ nm} - 1)/\text{Dispersion value} \quad (III)$$

(Abbe Number of Glass Fiber)

A glass plate with a size of 8 mm in width by 20 mm in length by 5 mm in thickness is prepared with the glass material constituting the glass fiber, the surface thereof is polished well, and the plate is measured for the refractive index at a wavelength of 589 nm in accordance with the JIS K 7142A method under the condition where the NAR-2T available from ATAGO CO., LTD. as an Abbe refractometer, diiodomethane as the contact liquid and the sodium D line with a wavelength of 589 nm as a light source are used and the measurement temperature is set to 23° C. Subsequently, natural light is used as a light source, a dispersion value is measured to be calculated, and the Abbe number is calculated according to the foregoing equation (III).

Since the transparent noncombustible sheet 1 according to the present invention has a high level of transparency and a high level of noncombustibility, and a visual field is effectively suppressed from being interrupted and the beautiful appearance is effectively suppressed from being impaired, the transparent noncombustible sheet 1 can be suitably used as a smoke-proof hanging wall, a smoke-proof sheet, a partition wall, a smoke-proof curtain, a touch panel or the like. In this connection, the noncombustibility of the transparent noncombustible sheet 1 according to the present invention refers to noncombustibility at a certain degree where, when the surface of the transparent noncombustible sheet 1 is irradiated with radiant heat of 50 kw/m$^2$ using a radiation electric heater, the total calorific value during a period of 20 minutes after the initiation of heating is less than or equal to 8 MJ/m$^2$ and the maximum heat generation rate does not exceed 200 kw/m$^2$ continuously for a period longer than or equal to 10 seconds during a period of 20 minutes after the initiation of heating.

The production method of the transparent noncombustible sheet 1 according to the present invention is not particularly limited, and examples thereof include the following production methods. First, a piece of glass fiber fabric 2 mentioned above and a resin composition mentioned above for constituting the cured resin composition layer 3 are prepared. Next, the glass fiber fabric 2 is applied with the resin composition mentioned above to be impregnated therewith, after which the thickness of the resin composition layer and the content are adjusted using a squeezing roller and the like. Next, the resin composition is cured by heating and the like to obtain the transparent noncombustible sheet 1 including the cured resin composition layer 3 prepared by allowing the glass fiber fabric 2 to be impregnated with the resin composition. Alternatively, two films of polyethylene terephthalate or the like onto which the resin composition mentioned above is applied are prepared, the two films are arranged on both faces of a piece of glass fiber fabric 2 and are press-bonded to allow the glass fiber fabric 2 to be impregnated with the resin composition from both face sides thereof, and the resin composition is cured, after which the films are peeled off to obtain the transparent noncombustible sheet 1 including the cured resin composition layer 3 prepared by allowing the glass fiber fabric 2 to be impregnated with the resin composition.

In the case where the resin composition is cured by heat energy, the heating temperature is not particularly limited, and for example, the temperature can be set to 50 to 200° C. or so. Moreover, in the case where the resin composition is cured by light energy, the resin composition is irradiated with light to be cured. With regard to the condition for the photoirradiation, for example, the integrated light quantity can be set to 100 to 500 mJ/cm$^2$.

In the case where the transparent noncombustible sheet 1 according to the present invention includes the film layer 4, on the cured resin composition layer 3 obtained as above, a resin film mentioned above constituting the film layer 4 is arranged, and then, can be heated and pressed with a press machine or the like to form the film layer 4 on the cured resin composition layer 3. Moreover, in the case where the transparent noncombustible sheet 1 further includes a net body layer 6 which is composed of a glass fiber net body and interposed between the cured resin composition layer 3 and the film layer 4, onto the cured resin composition layer 3, for example, an adhesive composed of a urethane-based resin and the like is applied, after which, on this, the glass fiber net body mentioned above constituting the net body layer 6 is arranged, and furthermore, on the glass fiber net body, a resin film mentioned above constituting the film layer 4 is arranged, and then, can be heated and pressed with a press machine or the like to form the net body layer 5 and the film layer 4 on the cured resin composition layer 3.

2. Construction Method of Transparent Noncombustible Sheet for Smoke-proof Hanging Wall The construction method of a transparent noncombustible sheet for a smoke-proof hanging wall according to the present invention is characterized as including step I of selecting a candidate sheet having prescribed total light transmittance and haze value, and step II of allowing the candidate sheet selected in the step I to be attached to and suspended down from the ceiling of a building. Hereinafter, the construction method of a transparent noncombustible sheet for a smoke-proof hanging wall according to the present invention will be described in detail.

In the construction method of a transparent noncombustible sheet for a smoke-proof hanging wall according to the present invention, transparent noncombustible sheets each of which includes glass fiber fabric and a cured resin composition layer prepared by allowing the glass fiber fabric to be impregnated with a resin composition are employed as candidate sheets. In this context, the candidate sheets refer to test subject sheets which are provided for the construction method of a transparent noncombustible sheet for a smoke-proof hanging wall according to the present invention in order to judge the appropriateness of sheets as the transparent noncombustible sheet for a smoke-proof hanging wall. The structure of the candidate sheet is not particularly limited as long as the sheet is a transparent noncombustible sheet which includes glass fiber fabric and a cured resin composition layer prepared by allowing the glass fiber fabric to be impregnated with a resin composition.

In the construction method of a transparent noncombustible sheet for a smoke-proof hanging wall according to the present invention, first, a transparent noncombustible sheet which includes the cured resin composition layer formed of a cured product of the resin composition containing a curable resin and a bifunctional (meth)acrylate, has a total light transmittance of the transparent noncombustible sheet of greater than or equal to 80% and has a haze value of the transparent noncombustible sheet or less than or equal to 30% is selected among the candidate sheets (step I). The measurement methods for the total light transmittance and haze are as described in the section of "1. Transparent noncombustible sheet".

Then, a candidate sheet selected in the step I is attached to and suspended down from the ceiling of a building (step II). The method of allowing a transparent noncombustible sheet to be attached to and suspended down from the ceiling of a building may be the same as a conventional construction method of a smoke-proof hanging wall.

The smoke-proof hanging wall thus constructed has high transparency, can suppress blurring and color bleeding, and can suppress interruption of the visual field.

3. Screening Method of Transparent Noncombustible Sheet for Smoke-proof Hanging Wall The screening method of a transparent noncombustible sheet for a smoke-proof hanging wall according to the present invention is characterized as including the first step of measuring the total light transmittance and the haze value and the second step of selecting a candidate sheet having prescribed total light transmittance and haze value. Hereinafter, the screening method of a transparent noncombustible sheet for a smoke-proof hanging wall according to the present invention will be described in detail.

In the screening method of a transparent noncombustible sheet for a smoke-proof hanging wall according to the present invention, transparent noncombustible sheets each of which includes glass fiber fabric and a cured resin composition layer prepared by allowing the glass fiber fabric to be impregnated with a resin composition, the cured resin composition layer being formed of a cured product of the resin composition containing a curable resin and a bifunctional (meth)acrylate are employed as candidate sheets. The candidate sheets are as described in the section of "2. Construction method of transparent noncombustible sheet for smoke-proof hanging wall".

In the screening method of a transparent noncombustible sheet for a smoke-proof hanging wall according to the present invention, first, with regard to the candidate sheets, the total light transmittance and the haze value are measured. The measurement methods for the total light transmittance and haze are as described in the section of "1. Transparent noncombustible sheet".

Then, on the basis of the measurement result of the first step, a candidate sheet which has a total light transmittance of greater than or equal to 80% and has a haze value of less than or equal to 30% is selected as a transparent noncombustible sheet for a smoke-proof hanging wall (the second step).

Since the transparent noncombustible sheet thus selected has high transparency and can suppress blurring and color bleeding, the sheet is utilized as a smoke-proof hanging wall that can suppress interruption of the visual field.

EXAMPLES

The present invention will be described below in detail with reference to Examples and Comparative example. However, the present invention is not limited to the Examples.

Examples 1 to 10 and Comparative Example 1

As glass fiber fabric, commercially available glass fiber fabric (glass material: E-glass, specific gravity 2.54 g/cm$^3$) described in Table 1 was cut into a piece of 200 mm×200 mm to be used. In this connection, in Table 1, each of "E03R SK", "E06C SK" and "E10T" is a trade name for E-glass fiber woven fabric available from UNITIKA LTD. The E-glass fiber woven fabric has been subjected to a heat treatment for removing an organic substance and a surface treatment with a silane coupling agent. In this connection, with regard to the glass material used in Examples 1 to 3, the glass volume fraction mentioned above was determined to be 39.4%.

As a resin composition with which the glass fiber fabric mentioned above is impregnated, a mixture of a vinyl ester resin (available from Japan U-Pica Company Ltd.), a styrene monomer (available from Japan U-Pica Company Ltd.), a bifunctional (meth)acrylate and a photopolymerization initiator, which are blended so as to have a composition described in Table 1, was used. In this connection, as the bifunctional (meth)acrylate which is a curing agent, NPGDA (neopentylglycol diacrylate, molecular weight 212, (available from Japan U-Pica Company Ltd.)), PEGDA with a molecular weight of about 300 (polyethylene glycol diacrylate, (available from Japan U-Pica Company Ltd.)) or PEGDA with a molecular weight of about 700 (polyethylene glycol diacrylate, (available from Japan U-Pica Company Ltd.)) described in Table 1 was used. Moreover, the amount of a photopolymerization initiator was set to 2 parts by mass based on 100 parts by mass of the total of a vinyl ester resin, a styrene monomer and a bifunctional (meth)acrylate.

First, onto a PET film with a thickness of 0.05 mm, a resin composition in an amount (g/m$^2$) described in Table 1 was applied. Next, on the resin composition, glass fiber fabric in an amount (g/m$^2$) described in Table 1 was mounted and allowed to settle for 1 minute, and interstices in the glass fiber fabric were impregnated with the resin mentioned above. Then, a PET film with a thickness of 0.05 mm was mounted thereon from above, and the film was pressed from above by a roller. Afterward, the resin composition accompanied by PET films mentioned above was subjected to photoirradiation (photoirradiation condition: integrated light quantity 200 mJ/cm$^2$) and the resin composition was cured to form a cured resin composition layer. Next, the PET films were removed to obtain a transparent noncombustible sheet with a thickness described in Table 1. In the obtained transparent noncombustible sheet, the interstices among glass fibers of the glass fiber fabric were impregnated with the resin composition, the cured resin composition layer (a cured product of the resin composition) was formed, and respective cured resin composition layer portions were formed on both faces of a layer of glass fiber fabric. In this connection, two pieces of glass fiber fabric in Examples 8 to 10 were arranged at two positions, which were calculated according to the equation (I) previously described, on respective surface sides of the cured resin composition layer. For example, in the case of Example 8 in Table 1, two pieces of glass fiber fabric are arranged at respective surface sides of the cured resin composition layer, and with regard to respective pieces of glass fiber fabric, the shortest distance $L_1$ from the surface of the cured resin composition layer to the center part N of the piece of glass fiber fabric and the thickness $L_0$ of the cured resin composition layer satisfy $L_1/L_0 \times 100 = 18\%$.

In this connection, in Examples and Comparative example, the fabric density of glass fiber woven fabric was measured and calculated according to JIS R 3420 2013 7.9. Moreover, the thickness of the piece of glass fiber woven fabric was measured and calculated according to the JIS R 3420 2013 7.10.1A method. The mass of the piece of glass fiber woven fabric was measured and calculated according to JIS R 3420 2013 7.2. The refractive indices of a cured resin composition and glass fiber woven fabric were measured and calculated by a method mentioned above. The following evaluation was performed after a transparent noncombustible sheet was produced and then allowed to stand for 1 week in a room.

(Position of Glass Fiber Fabric)

Respective transparent noncombustible sheets obtained in Examples 1 to 10 and Comparative Example 1 were observed with a scanning electron microscope, and the position of glass fiber fabric (%) was calculated according to the equation (I) previously described.

(Evaluation for Noncombustibility)

The surface of each of the respective transparent noncombustible sheets obtained in Examples 1 to 10 and Comparative Example 1 was irradiated with radiant heat of 50 kw/m$^2$ using a radiation electric heater, and the total calorific value during a period of 20 minutes after the initiation of heating and the period of time during which the calorific value exceeded 200 kw/m$^2$ during a period of 20 minutes after the initiation of heating were measured. In the case where the total calorific value during a period of 20 minutes after the initiation of heating was less than or equal to 8 MJ/m$^2$ and the maximum heat generation rate did not exceed 200 kw/m$^2$ continuously for a period longer than or equal to 10 seconds during a period of 20 minutes after the initiation of heating, the transparent noncombustible sheet was evaluated as being excellent in noncombustibility.

(Evaluation for Blurring)

A thousand yen note was placed on top of a desk, a transparent noncombustible sheet was held in place at a distance of about 50 cm above the thousand yen note, and the thousand yen note was observed through the transparent noncombustible sheet from a point at a distance of 10 cm above the transparent noncombustible sheet to evaluate whether or not characters of "Thousand yen", "Bank of Japan note" and the serial number were clearly readable. The evaluation criteria are as follows. In the present invention, from the viewpoint of practicality, a transparent noncombustible sheet evaluated as not less than 2 was regarded as acceptable. The results are shown in Table 1.

5 . . . All characters of "Thousand yen", "Bank of Japan note" and the serial number were clearly readable.

4 . . . Only characters of "Thousand yen" and "Bank of Japan note" were clearly readable.

3 . . . Only characters of "Thousand yen" were clearly readable.

2 . . . Only characters of "Thousand yen" were legible but not clearly readable.

1 . . . No characters were legible and not clearly readable.

(Evaluation for Color Bleeding)

A fluorescent lamp was viewed through each of the respective transparent noncombustible sheets to evaluate whether or not the color bleeding around the fluorescent lamp was conspicuous. The evaluation criteria are as follows. In the present invention, from the viewpoint of practicality, a transparent noncombustible sheet evaluated as not less than 3 was regarded as acceptable. The results are shown in Table 1.

5 . . . The color bleeding around the fluorescent lamp was almost inconspicuous.

4 . . . The color bleeding around the fluorescent lamp was slightly viewed but was hardly conspicuous.

3 . . . The color bleeding around the fluorescent lamp was viewed and was conspicuous to some extent.

2 . . . The color bleeding around the fluorescent lamp was conspicuous.

1 . . . The color bleeding around the fluorescent lamp was very conspicuous and the feeling of transparency was impaired.

(Total Light Transmittance and Haze)

The total light transmittance and haze of each of the respective transparent noncombustible sheets were measured according to JIS K7375 2008 "Plastics—Determination of total luminous transmittance and reflectance".

(Hardness of Transparent Noncombustible Sheet)

By 5 panelists, the sensory evaluation was performed for the hardness. An external force was applied to a transparent noncombustible sheet by hand, and the hardness thereof was evaluated based on 5 grades in the order from a sheet giving the strongest feeling of hardness to calculate an average point of 5 respondents. A transparent noncombustible sheet evaluated as not less than 2 points was regarded as acceptable.

(Warpage of Transparent Noncombustible Sheet)

A transparent noncombustible sheet was subjected to a heat treatment under the condition of 100° C. in a dryer for 3 minutes, after which the sheet was observed for the warpage to be evaluated according to the following criteria.

⊙ . . . No warpage was generated.

○ . . . Warpage was slightly generated but at a level causing no practical problem.

Δ . . . Warpage was somewhat large at a level slightly causing a practical problem.

x . . . Warpage was considerably large at a level causing a practical problem.

The results are shown in Table 1.

TABLE 1

| | | Example 1 | Example 2 | Example 3 | Example 4 | Example 5 | Example 6 | Example 7 | Example 8 | Example 9 | Example 10 | Comparative Example 1 |
|---|---|---|---|---|---|---|---|---|---|---|---|---|
| Resin composition | Composition (% by mass) Vinyl ester resin | 50 | 60 | 50 | 50 | 50 | 50 | 60 | 60 | 60 | 60 | 50 |
| | Styrene monomer | 25 | 20 | 25 | 25 | 25 | 25 | 20 | 20 | 20 | 20 | 50 |
| | NPGDA (Molecular weight 212) | 25 | 20 | 25 | 25 | 0 | 0 | 20 | 20 | 20 | 20 | 0 |
| | PEGDA (Molecular weight about 300) | 0 | 0 | 0 | 0 | 25 | 0 | 0 | 0 | 0 | 0 | 0 |
| | PEGDA (Molecular weight about 700) | 0 | 0 | 0 | 0 | 0 | 25 | 0 | 0 | 0 | 0 | 0 |
| | Refractive index | 1.563 | 1.563 | 1.563 | 1.563 | 1.563 | 1.563 | 1.563 | 1.563 | 1.563 | 1.563 | 1.58 |
| Glass fiber fabric | Mass (g/m²) | 90 | 90 | 54 | 168 | 45 | 45 | 100 | 180 | 180 | 180 | 45 |
| | Cloth article number | E03R SK | E03R SK | E06C SK | E10T | E03R SK | E03R SK | E03R SK | E03R SK | E03R SK | E03R SK | E03R SK |
| | Kind of warp yarn | ECC1200 1/0 1Z | ECC1200 1/0 1Z | ECD450 1/0 0.8Z | ECE225 1/0 0.7Z | ECC1200 1/0 1Z | ECC1200 1/0 1Z | ECC1200 1/0 1Z | ECC1200 1/0 1Z | ECC1200 1/0 1Z | ECC1200 1/0 1Z | ECC1200 1/0 1Z |
| | Kind of weft yarn | ECC1200 1/0 1Z | ECC1200 1/0 1Z | ECD450 1/0 0.8Z | ECE225 1/0 0.7Z | ECC1200 1/0 1Z | ECC1200 1/0 1Z | ECC1200 1/0 1Z | ECC1200 1/0 1Z | ECC1200 1/0 1Z | ECC1200 1/0 1Z | ECC1200 1/0 1Z |
| | Warp yarn density (number of yarns/2.54 cm) | 90 | 90 | 60 | 60 | 90 | 90 | 90 | 90 | 90 | 90 | 90 |
| | Weft yarn density (number of yarns/2.54 cm) | 90 | 90 | 60 | 58 | 90 | 90 | 90 | 90 | 90 | 90 | 90 |
| | Thickness (μm) | 30 | 30 | 50 | 90 | 30 | 30 | 30 | 30 | 30 | 30 | 30 |
| | Way of weaving | Plain weave | Plain weave | Plain weave | Plain weave | Plain weave | Plain weave | Plain weave | Plain weave | Plain weave | Plain weave | Plain weave |
| | Refractive index | 1.561 | 1.561 | 1.561 | 1.561 | 1.561 | 1.561 | 1.561 | 1.561 | 1.561 | 1.561 | 1.561 |
| | Mass (g/m²) per one piece of glass fiber fabric | 30 | 30 | 50 | 106 | 30 | 30 | 30 | 30 | 30 | 30 | 30 |
| | Number of pieces of glass fiber fabric | 1 | 1 | 1 | 1 | 1 | 1 | 1 | 2 | 2 | 2 | 1 |
| | Position of glass fiber fabric (%) | 50 | 50 | 50 | 50 | 50 | 50 | 50 | 18, 18 | 18, 50 | 42, 42 | 50 |
| | Photopolymerization initiator (g/m²) | 1.8 | 1.8 | 1.1 | 3.4 | 0.9 | 0.9 | 1.8 | 3.6 | 3.6 | 3.6 | 0.9 |
| Evaluation | Thickness (μm) | 110 | 110 | 70 | 180 | 50 | 50 | 120 | 180 | 180 | 180 | 50 |
| | Blurring | 4 | 5 | 4 | 4 | 2 | 2 | 5 | 5 | 5 | 5 | 1 |
| | Color bleeding | 5 | 5 | 4 | 3 | 4 | 4 | 5 | 5 | 5 | 5 | 1 |
| | Total light transmittance of transparent sheet (%) | 90 | 90 | 91.6 | 90.4 | 90 | 90 | 90 | 90 | 90 | 90 | 85 |
| | Haze of transparent sheet (%) | 2 | 2 | 2 | 3 | 2 | 2 | 2 | 2 | 2 | 2 | 20 |
| | Evaluation for noncombustibility | ⊙ | ⊙ | ⊙ | ⊙ | ⊙ | ⊙ | ⊙ | ⊙ | ⊙ | ⊙ | ⊙ |
| | Hardness | 2 | 2 | 2 | 3 | 2 | 2 | 2 | 5 | 3 | 3 | 2 |
| | Warpage | ○ | ○ | ○ | ○ | ○ | ○ | ○ | ○ | ○ | ○ | ○ |

As shown in Table 1, blurring and color bleeding were suppressed in Examples 1 to 10 where a bifunctional (meth)acrylate was used for the resin composition, and it has become apparent that the sheet can be suitably used as a smoke-proof hanging wall or the like. In particular, in Examples 1 to 4 where the molecular weight of the bifunctional (meth)acrylate was less than or equal to 250, the sheet was excellent especially in inhibitory effect on blurring. Furthermore, in Example 2 where the molecular weight of the bifunctional (meth)acrylate was less than or equal to 250, the content thereof was set to 20% by mass and the proportion of a curable resin was set to 60% by mass, the sheet was excellent especially in inhibitory effect on blurring as compared with that in Example 1. Moreover, in comparison between Examples 1 and 2 and Example 3, the sheet in Examples 1 and 2 where the fiber diameter was smaller than that in Example 3 and the mass ratio of the glass fiber was within the range of 20 to 28% by mass was more excellent in inhibitory effect on color bleeding than that in Example 3. On the other hand, in Example 4, since the fiber diameter of the glass fiber was large, the sheet was slightly low in inhibitory effect on color bleeding. Moreover, in Examples 5 and 6 where the molecular weight of the bifunctional (meth)acrylate was greater than 250, the sheet was slightly poor in inhibitory effect on blurring. In Example 8, since two pieces of glass fiber fabric were included at two respective positions satisfying the above-mentioned equation (I) in both surface parts of the cured resin composition layer, the sheet was excellent especially in inhibitory effect on blurring and color bleeding and the sheet was hard and had no occurrence of warpage. On the other hand, in a transparent noncombustible sheet of Comparative Example 1 where a bifunctional (meth)acrylate was not used, the sheet was excellent in total light transmittance but was very poor in inhibitory effect on blurring and color bleeding, and it has become apparent that the sheet is not suitable as a smoke-proof hanging wall or the like. In Comparative Example 1, a transparent noncombustible sheet was prepared by a method corresponding to that in Example of Patent Document 1, but the sheet was very poor in inhibitory effect on blurring and color bleeding, and it has become apparent that the sheet is not suitable as a smoke-proof hanging wall or the like.

DESCRIPTION OF REFERENCE SIGNS

1: Transparent noncombustible sheet
2: Glass fiber fabric
3: Cured resin composition layer
4: Film layer
5: Net body layer

The invention claimed is:

1. A transparent noncombustible sheet comprising glass fiber fabric and a cured resin composition layer prepared by allowing the glass fiber fabric to be impregnated with a resin composition,
wherein the cured resin composition layer is formed of a cured product of the resin composition containing a curable resin and a bifunctional (meth)acrylate,
two pieces of glass fiber fabric are arranged at respective surface sides of the cured resin composition layer while the center part in the thickness direction of the piece of glass fiber fabric is positioned nearer to the surface side than the center part in the thickness direction of the cured resin composition layer, wherein each piece of glass fiber fabric comprises a warp and a weft;
the proportion of the glass fiber fabric in the total amount of the glass fiber fabric and the cured resin composition layer is 20 to 50% by mass,
the total light transmittance of the transparent noncombustible sheet is greater than or equal to 80%, and
the haze value of the transparent noncombustible sheet is less than or equal to 30%.

2. The transparent noncombustible sheet according to claim 1, wherein the bifunctional (meth)acrylate is a di(meth)acrylate of an alkylene diol with 1 to 6 carbon atoms.

3. The transparent noncombustible sheet according to claim 1, wherein the molecular weight of the bifunctional (meth)acrylate is less than or equal to 250.

4. The transparent noncombustible sheet according to claim 3, wherein the molecular weight of the bifunctional (meth)acrylate is greater than or equal to 150.

5. The transparent noncombustible sheet according to any one of claims 1 to 4, wherein the resin composition contains a styrene monomer.

6. The transparent noncombustible sheet according to claim 1, wherein the resin composition is photocurable.

7. The transparent noncombustible sheet according to claim 1, wherein the resin composition contains 40 to 80% by mass of the curable resin and 10 to 40% by mass of the bifunctional (meth)acrylate.

8. The transparent noncombustible sheet according to claim 1, wherein the resin composition contains 60 to 80% by mass of the curable resin and 10 to 20% by mass of the bifunctional (meth)acrylate.

9. The transparent noncombustible sheet according to claim 1, wherein the proportion of the glass fiber fabric in the total amount of the glass fiber fabric and the cured resin composition layer is 20 to 28% by mass.

10. The transparent noncombustible sheet according to claim 1, further comprising a film layer disposed on the cured resin composition layer.

11. The transparent noncombustible sheet according to claim 10, further comprising a net body layer which is composed of a glass fiber net body and interposed between the cured resin composition layer and the film layer.

12. The transparent noncombustible sheet according to claim 1, wherein the transparent noncombustible sheet has a thickness of 40 to 400 μm.

13. The transparent noncombustible sheet according to claim 1, wherein a plurality of pieces of glass fiber fabric are included in the identical cured resin composition layer, at least two pieces of glass fiber fabric among the plurality of pieces of glass fiber fabric are arranged at least at respective surface sides of the cured resin composition layer, and the two pieces of glass fiber fabric are included at respective surface sides of the cured resin composition layer while the shortest distance $L_1$ from the surface of the cured resin composition layer to the center part of the piece of glass fiber fabric and the thickness $L_0$ of the cured resin composition layer satisfy the relationship of the following equation (I):

$$0(\%) < L_1/L_0 \times 100 < 30(\%) \qquad (I).$$

14. A smoke-proof hanging wall comprising the transparent noncombustible sheet according to claim 1.

15. A smoke-proof shutter comprising the transparent noncombustible sheet according to claim 1.

16. A partition wall comprising the transparent noncombustible sheet according to claim 1.

17. A smoke-proof curtain comprising the transparent noncombustible sheet according to claim 1.

18. A touch panel comprising the transparent noncombustible sheet according to claim 1.

* * * * *